(12) United States Patent
Burkholz et al.

(10) Patent No.: US 11,344,220 B2
(45) Date of Patent: May 31, 2022

(54) INVASIVE MEDICAL DEVICE COVER WITH MAGNET

(71) Applicant: Becton, Dickinson and Company, Franklin Lakes, NJ (US)

(72) Inventors: Jonathan Karl Burkholz, Salt Lake City, UT (US); Weston Harding, Lehi, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 590 days.

(21) Appl. No.: 15/154,353

(22) Filed: May 13, 2016

(65) Prior Publication Data
US 2017/0325713 A1   Nov. 16, 2017

(51) Int. Cl.
*A61B 5/06*     (2006.01)
*A61M 5/32*     (2006.01)
*A61M 5/158*    (2006.01)
*A61M 25/01*    (2006.01)
*A61M 25/06*    (2006.01)
*A61B 17/34*    (2006.01)
*A61B 17/00*    (2006.01)
(Continued)

(52) U.S. Cl.
CPC .............. *A61B 5/062* (2013.01); *A61M 5/158* (2013.01); *A61M 5/32* (2013.01); *A61M 5/3202* (2013.01); *A61M 25/0158* (2013.01); *A61M 25/065* (2013.01); *A61B 17/3403* (2013.01); *A61B 2017/00876* (2013.01); *A61B 2090/3954* (2016.02); *A61M 5/427* (2013.01); *A61M 2005/1585* (2013.01); *A61M 2205/0272* (2013.01); *A61M 2205/0288* (2013.01)

(58) Field of Classification Search
CPC ......... A61B 5/062; A61M 5/158; A61M 5/32; A61M 5/3202; A61M 25/0158; A61M 25/065
USPC ....................................................... 600/567
See application file for complete search history.

(56) References Cited

U.S. PATENT DOCUMENTS 3,063,419 A   11/1962   Parker
3,789,336 A   1/1974    Gordin
4,161,943 A   7/1979    Nogier
(Continued)

FOREIGN PATENT DOCUMENTS

CN   201138912 Y   10/2008
CN   104853799 A   8/2015
(Continued)

OTHER PUBLICATIONS

PCT International Search Report and Written Opinion in PCT/US2017/031566 dated Aug. 14, 2017, 17 pages.
(Continued)

*Primary Examiner* — Daniel L Cerioni
(74) *Attorney, Agent, or Firm* — Servilla Whitney LLC (57) ABSTRACT

A cover for magnetizing a shaft of a tissue-penetrating medical device is disclosed including a sleeve member having a hollow body to form a protective closure over the shaft of the tissue-penetrating medical device. The open end of the hollow body provides a receiving space for receiving the shaft of the tissue-penetrating medical device. A magnet is disposed on the sleeve member. Medical devices and methods of magnetizing the shaft of a tissue-penetrating medical device using the cover are also disclosed.

8 Claims, 6 Drawing Sheets

(51) Int. Cl.
*A61M 5/42* (2006.01)
*A61B 90/00* (2016.01)

(56) References Cited

U.S. PATENT DOCUMENTS

| | | | |
|---|---|---|---|
| 4,484,814 A | 11/1984 | Kawaguchi et al. | |
| 4,813,729 A | 3/1989 | Speckhart | |
| 5,000,912 A | 3/1991 | Bendel et al. | |
| 5,359,992 A * | 11/1994 | Hori | A61B 1/00188 126/4 |
| 5,431,640 A | 7/1995 | Gabriel | |
| 5,461,311 A | 10/1995 | Nakazato et al. | |
| 5,471,186 A | 11/1995 | Seo | |
| 5,691,681 A | 11/1997 | Okugawa | |
| 5,955,881 A | 9/1999 | White et al. | |
| 6,004,294 A | 12/1999 | Brimhall et al. | |
| 6,158,157 A | 12/2000 | Hiscock et al. | |
| 6,203,526 B1 | 3/2001 | McBeth et al. | |
| 6,228,062 B1 | 5/2001 | Howell et al. | |
| 6,263,230 B1 | 7/2001 | Haynor et al. | |
| 6,310,532 B1 | 10/2001 | Santa Cruz et al. | |
| 6,379,333 B1 | 4/2002 | Brimhall et al. | |
| 6,432,036 B1 | 8/2002 | Kim | |
| 6,471,273 B1 | 10/2002 | Friedrich et al. | |
| 6,475,226 B1 | 11/2002 | Belef et al. | |
| 6,663,555 B2 | 12/2003 | Mitchiner et al. | |
| 6,749,588 B1 | 6/2004 | Howell et al. | |
| 7,935,080 B2 | 5/2011 | Howell et al. | |
| 8,226,540 B1 | 7/2012 | Chi | |
| 8,485,992 B2 | 7/2013 | Griffin et al. | |
| 8,895,859 B2 | 11/2014 | Koniers | |
| RE45,896 E | 2/2016 | Stout et al. | |
| 9,314,201 B2 | 4/2016 | Burkholz et al. | |
| 9,616,214 B2 | 4/2017 | Stout et al. | |
| 9,802,009 B2 | 10/2017 | Nessel et al. | |
| 2002/0042581 A1* | 4/2002 | Cervi | A61B 10/025 600/567 |
| 2002/0193756 A1 | 12/2002 | Prindle | |
| 2003/0100829 A1 | 5/2003 | Zhong | |
| 2003/0199791 A1* | 10/2003 | Boecker | A61B 5/150167 600/576 |
| 2004/0023628 A1 | 11/2004 | Howell et al. | |
| 2004/0249428 A1 | 12/2004 | Wang et al. | |
| 2005/0004417 A1 | 1/2005 | Nelson et al. | |
| 2005/0065472 A1 | 3/2005 | Cindrich et al. | |
| 2005/0080378 A1 | 4/2005 | Cindrich et al. | |
| 2005/0165301 A1 | 7/2005 | Smith et al. | |
| 2005/0192535 A1 | 9/2005 | Takagi et al. | |
| 2005/0217685 A1 | 10/2005 | Burkholz et al. | |
| 2007/0049846 A1 | 3/2007 | Bown et al. | |
| 2007/0255211 A1 | 11/2007 | Young | |
| 2008/0065025 A1 | 3/2008 | Jenkins et al. | |
| 2008/0086097 A1 | 4/2008 | Rasmussen et al. | |
| 2008/0200903 A1 | 8/2008 | Christensen et al. | |
| 2008/0200904 A1 | 8/2008 | Cluff et al. | |
| 2008/0287906 A1 | 11/2008 | Burkholz et al. | |
| 2009/0012517 A1 | 1/2009 | de la Rama et al. | |
| 2009/0032499 A1 | 2/2009 | Tenne et al. | |
| 2009/0088696 A1 | 4/2009 | Harding et al. | |
| 2009/0163871 A1 | 6/2009 | Burkholz et al. | |
| 2009/0281481 A1 | 11/2009 | Harding et al. | |
| 2009/0281499 A1 | 11/2009 | Harding et al. | |
| 2009/0281525 A1 | 11/2009 | Harding et al. | |
| 2009/0287154 A1 | 11/2009 | Harding et al. | |
| 2009/0292243 A1 | 11/2009 | Harding et al. | |
| 2010/0036238 A1 | 2/2010 | Neidert et al. | |
| 2010/0204648 A1 | 8/2010 | Stout et al. | |
| 2010/0204660 A1 | 8/2010 | McKinnon et al. | |
| 2010/0217275 A1 | 8/2010 | Carmeli et al. | |
| 2010/0222746 A1 | 9/2010 | Burkholz | |
| 2010/0228119 A1 | 9/2010 | Brennan et al. | |
| 2011/0046570 A1 | 2/2011 | Stout et al. | |
| 2011/0066121 A1 | 3/2011 | Hoang et al. | |
| 2011/0160662 A1 | 6/2011 | Stout et al. | |
| 2011/0160663 A1 | 6/2011 | Stout et al. | |
| 2011/0196397 A1 | 8/2011 | Frantz et al. | |
| 2011/0222299 A1 | 9/2011 | Takahashi et al. | |
| 2011/0267043 A1 | 11/2011 | Dolsak | |
| 2012/0016316 A1 | 1/2012 | Zhuang et al. | |
| 2012/0041297 A1 | 2/2012 | McGary | |
| 2012/0053523 A1 | 3/2012 | Harding | |
| 2012/0126842 A1* | 5/2012 | Huang | G01R 1/06788 324/755.11 |
| 2012/0023249 A1 | 9/2012 | Ma et al. | |
| 2012/0232499 A1 | 9/2012 | Stout et al. | |
| 2013/0035646 A1 | 2/2013 | Liversidge | |
| 2013/0075649 A1 | 3/2013 | Wang | |
| 2013/0090608 A1 | 4/2013 | Stout et al. | |
| 2013/0131547 A1* | 5/2013 | Hardert | A61B 10/0266 600/567 |
| 2013/0165867 A1 | 6/2013 | Isaacson et al. | |
| 2013/0165868 A1 | 6/2013 | Isaacson et al. | |
| 2013/0210808 A1 | 11/2013 | Stout et al. | |
| 2014/0031674 A1 | 1/2014 | Newman et al. | |
| 2014/0039399 A1 | 2/2014 | Burkholz | |
| 2014/0046261 A1 | 2/2014 | Newman et al. | |
| 2014/0074028 A1 | 3/2014 | Sonderegger et al. | |
| 2014/0128674 A1 | 5/2014 | Wieters | |
| 2014/0135595 A1 | 5/2014 | Powell et al. | |
| 2014/0150911 A1 | 6/2014 | Hanner et al. | |
| 2014/0180328 A1 | 6/2014 | Vaccaro et al. | |
| 2014/0228775 A1 | 8/2014 | Burkholz et al. | |
| 2014/0253270 A1 | 9/2014 | Nicholls et al. | |
| 2014/0257080 A1 | 9/2014 | Dunbar et al. | |
| 2014/0257234 A1 | 9/2014 | Ma et al. | |
| 2014/0276462 A1 | 9/2014 | Vincent et al. | |
| 2014/0276539 A1 | 9/2014 | Allison et al. | |
| 2014/0323988 A1 | 10/2014 | Magnani et al. | |
| 2014/0364809 A1 | 12/2014 | Isaacson et al. | |
| 2015/0038910 A1 | 2/2015 | Harding et al. | |
| 2015/0080710 A1 | 3/2015 | Henkel et al. | |
| 2015/0202421 A1 | 7/2015 | Ma et al. | |
| 2015/0202422 A1 | 7/2015 | Ma et al. | |
| 2015/0231307 A1 | 8/2015 | Shevgoor et al. | |
| 2015/0231309 A1 | 8/2015 | Bihlmaier et al. | |
| 2015/0253401 A1 | 9/2015 | Rapoport | |
| 2015/0306319 A1 | 10/2015 | Nessel et al. | |
| 2015/0306369 A1 | 10/2015 | Burkholz et al. | |
| 2015/0320977 A1 | 11/2015 | Vitullo et al. | |
| 2015/0359991 A1 | 12/2015 | Dunbar et al. | |
| 2016/0008517 A1 | 1/2016 | Burkholz et al. | |
| 2016/0008538 A1 | 1/2016 | Isaacson et al. | |
| 2016/0008569 A1 | 1/2016 | Harding | |
| 2016/0008579 A1 | 1/2016 | Burkholz et al. | |
| 2016/0008582 A1 | 1/2016 | Burkholz et al. | |
| 2016/0193453 A1 | 7/2016 | Isaacson et al. | |
| 2016/0361519 A1 | 12/2016 | Teoh et al. | |
| 2017/0035992 A1 | 2/2017 | Harding et al. | |
| 2017/0065750 A1 | 3/2017 | Ma et al. | |
| 2017/0087297 A1 | 3/2017 | Hanner et al. | |
| 2017/0100576 A1 | 4/2017 | Stout et al. | |
| 2017/0120008 A1 | 5/2017 | Burkholz et al. | |
| 2017/0120011 A1 | 5/2017 | Burkholz et al. | |
| 2017/0120014 A1 | 5/2017 | Harding et al. | |
| 2017/0120015 A1 | 5/2017 | Burkholz et al. | |
| 2017/0120016 A1 | 5/2017 | Burkholz et al. | |
| 2017/0120017 A1 | 5/2017 | Burkholz et al. | |
| 2017/0128712 A1 | 5/2017 | Harding et al. | |
| 2017/0232204 A1* | 8/2017 | Knapp | A61M 5/28 604/66 |

FOREIGN PATENT DOCUMENTS

| | | |
|---|---|---|
| EP | 0320623 A1 | 6/1989 |
| EP | 2730306 A2 | 5/2014 |
| JP | S5816599 A | 1/1983 |
| JP | S61160998 A | 7/1986 |
| JP | 2002119589 A | 4/2002 |
| JP | 2014501143 A | 1/2014 |
| JP | 2015535714 A | 12/2015 |
| WO | 02/083208 A2 | 10/2002 |
| WO | 2009061860 A1 | 5/2009 |
| WO | 2013034175 A1 | 3/2013 |

(56) References Cited

FOREIGN PATENT DOCUMENTS

| WO | 2013142386 A1 | 9/2013 |
|----|---------------|--------|
| WO | 2014052894 A2 | 4/2014 |
| WO | 2014072238 A1 | 5/2014 |

OTHER PUBLICATIONS

PCT International Search Report and Written Opinion in PCT/US2017/031572 dated Aug. 24, 2017, 14 pages.
Non-Final Office Action in U.S. Appl. No. 15/154,348 dated Jun. 7, 2018, 14 pages.
PCT International Preliminary Report on Patentability in PCT/US2017/031566 dated Nov. 22, 2018, 11 pages.
PCT International Preliminary Report on Patentability in PCT/US2017/031572 dated Nov. 22, 2018, 8 pages.
Final Office Action in U.S. Appl. No. 15/154,348, dated Mar. 22, 2019, 9 pages.
Final Office Action in U.S. Appl. No. 15/170,497 dated Sep. 16, 2019, 53 pages.
Non-Final Office Action in U.S. Appl. No. 15/154,348 dated Oct. 2, 2019, 10 pages.
Non-Final Office Action in U.S. Appl. No. 15/170,531 dated Sep. 6, 2019, 41 pages.
Non-Final Office Action in U.S. Appl. No. 15/604,244 dated Jun. 27, 2019, 50 pages.
Honnegowda, Lakshmisha, et al., "Security Enhancement for Magnetic Data Transaction in Electronic Payment and Healthcare Systems [online]", IACSIT International Journal of Engineering and Technology, Apr. 2013 [retrieved on Sep. 5, 2019], vol. 5, No. 2.
Final Office Action in U.S. Appl. No. 15/170,518 dated Nov. 7, 2019, 31 pages.
Final Office Action in U.S. Appl. No. 15/604,244 dated Jan. 10, 2020, 62 pages.
Nave, R., "Ferromagnetism [online], Georgia State University, HyperPhysics, Jul. 1, 2006 [retrieved on Oct. 12, 2018].", Retrieved from the internet: <URL: https://web.archive.org/web/20060701023036/http://hyperphysics.phyastr.gsu.edu/hbase/Solids/ferro.html>, 1 page.
Bhattacharya, Deepamala, "ALNICO [online], Chemistry Learner, May 31, 2014", [retrieved on Mar. 2, 2020], Retrieved from the Internet: <URL: https://web.archive.Org/web/20140531135446/http://www.chemistrylearner.com/alnico.html>. (Year: 2014).
Non-Final Office Action in U.S. Appl. No. 15/170,531, dated Sep. 18, 2020, 39 pages.
Non-Final Office Action in U.S. Appl. No. 15/604,244 dated Sep. 15, 2020, 97 pages.
Final Office Action in U.S. Appl. No. 15/170,497 dated Jun. 23, 2020, 40 pages.
Jiles, D., "Introduction to Magnetism and Magnetic Materials, Second Edition", CRC press, 1998. ISBN 0412798603, 9780412798603, p. 354.
"Final Office Action in U.S. Appl. No. 15/154,348 dated May 15, 2020, 9 pages".
"Final Office Action in U.S. Appl. No. 15/154,353 dated Jun. 24, 2020, 12 pages".
"Non-Final Office Action in U.S. Appl. No. 15/154,353 dated Jan. 13, 2021, 12 pages".
"Non-Final Office Action in U.S. Appl. No. 15/154,353 dated Mar. 17, 2020, 12 pages".
"Non-Final Office Action in U.S. Appl. No. 15/170,497 dated Jan. 24, 2020, 47 pages".
"PCT International Preliminary Report on Patentability in PCT/US2017/048997 dated Mar. 14, 2019, 9 pages".
"PCT International Search Report & Written Opinion in PCT/US2017/048997, dated Nov. 22, 2017", 15 pgs.
"PCT International Search Report and Written Opinion in PCT/US2017/031569 dated Aug. 28, 2017, 17 pages".
"Final Office Action in U.S. Appl. No. 15/170,531 dated Mar. 17, 2020, 37 pages".
"Non-Final Office Action in U.S. Appl. No. 15/170,497 dated Dec. 31, 2020, 37 pages".

* cited by examiner

INVASIVE MEDICAL DEVICE COVER WITH MAGNET

FIELD

Aspects of the present disclosure relate to a cover for magnetizing a tissue-penetrating medical device.

BACKGROUND

Traditionally, penetration of an invasive medical device such as a needle and catheter tubing through skin tissue to reach the vein during catheter insertion is invisible to clinicians. For this reason, clinicians must rely on their first-hand experience with needle insertion in combination with tactile sense to successfully identify the location of the vein. This may be a difficult task when attempting to access a small vein in a deep location under the skin, increasing risk of excess pain and/or injury to the patient. There are similar problems with insertion of other invasive medical devices such as guidewires, catheters, introducer needles, stylets, scalpel and guidewire with respect to the inability to precisely visualize the location of the invasive medical device.

Emerging procedural guidance systems utilize a combination of ultrasound and magnetic technologies to provide visualization of subdermal anatomy and device position in the in-plane and out-of-plane orientations. This combination of ultrasound and magnetic methods also allows for the projection or anticipation of the insertion device position relative to the patient's anatomy, and thereby improves the likelihood of successfully accessing the vascular and completing the invasive procedure.

Figure 1:
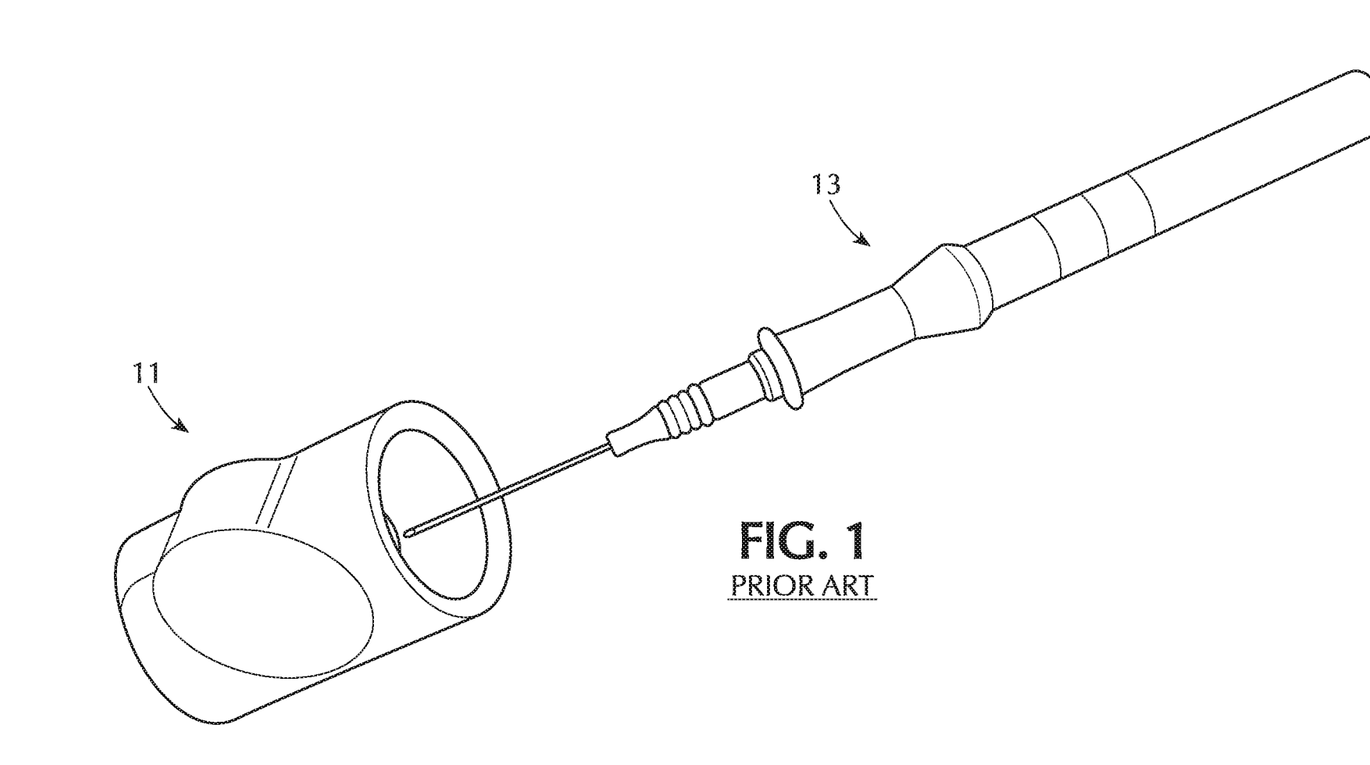
FIG. 1 shows a perspective view of a prior art disposable needle magnetizer.

One leading technology targets the a portion of the device that is inserted into the patient, e.g., the needle cannula, as the portion of the invasive device for magnetization, while another leading technology uses a permanent magnet located on the hub (e.g., needle hub) of the device. Current needle guidance systems typically utilize a magnetic field generated by magnetizing the needle by burying the needle into a magnetizer until the point of the needle hits a rubber stopping surface. FIG. 1 shows a perspective view of a currently available disposable needle magnetizer 11. As shown in FIG. 1, current practice uses an unprotected needle 13 that is placed within the external disposable needle magnetizer 11 to a depth defined by the bottom of the magnetizer. The current devices for magnetizing a needle prior to insertion generally are not sterile, not disposable, and not electronic.

In systems of the type shown in FIG. 1, damage to the needle can occur that is not apparent to the user that can negatively affect the insertion process. Also, the step of the user actively magnetizing the metal cannula has some limitations and inherent risks as this approach does not guarantee consistent magnetization since variability in clinician procedures such as depth of insertion, speed of process, and centering of the needle in the magnetizer will result in different degrees of magnetization. Considering the potential inconsistency of a user fully inserting the needle to the bottom of the magnetizer 11, the significant risk of damaging the needle tip, and the increased potential for contamination during this step, it would be advantageous to have a system that passively and consistently magnetizes the needle without introducing the aforementioned additional risks, such as needle tip damage and increased potential for contamination. Thus, there is a need for a system that passively and consistently magnetizes invasive medical devices while reducing or eliminating risks, such as needle tip damage and needle contamination.

SUMMARY

A first aspect of the disclosure pertains to a cover for magnetizing a tissue-penetrating medical device. A first embodiment pertains to a cover comprising a sleeve member having a hollow body, the hollow body having a distal end and a proximal end to form a protective closure over a portion (e.g., a shaft) of a tissue-penetrating medical device. In one or more embodiments, the sleeve member may have a length to cover the shaft of the tissue-penetrating medical device, and there are one or more magnets disposed on the sleeve member. In one or more embodiments, the open end of the hollow tubular body provides a receiving space for receiving at least a portion (e.g., the shaft) of the tissue-penetrating medical device.

In one or more embodiments, the device-receiving space permits movement of the tissue-penetrating medical device into and out of the device-receiving space. In one or more embodiments, the device-receiving space permits movement of the tissue-penetrating medical device in a parallel direction to the longitudinal axis of the tissue-penetrating medical device.

In one or more embodiments, one or more magnets are provided on one side of the device-receiving space. In one or more embodiments, two or more magnets are provided, with the two magnets disposed around the device-receiving space. According to one or more embodiments, the two or more magnets are disposed in slots positioned around the sleeve member. In one or more embodiments, the slots positioned around the sleeve member surround the device-receiving space.

In one or more embodiments, the cover may be sterile. In one or more embodiments, the cover may be disposable. In one or more embodiments, the cover may be both sterile and disposable. In one or more embodiments, the cover is plastic.

In one or more embodiments, the tissue-penetrating medical device may be a needle, cannula, stylet, catheter, scalpel or guidewire. According to one more embodiments, the cover passively magnetizes the tissue-penetrating medical device upon removal of the tissue-penetrating medical device from the cover. In a specific embodiments, the tissue-penetrating medical device is a needle, which, when magnetized is adapted for use with a procedural guidance system which can locate and project the position of the needle during an invasive medical procedure.

In one or more embodiments, the distal end of the tissue penetrating device includes a notch to provide immediate confirmation of vessel entry at a point of insertion.

A second aspect of the disclosure pertains to a medical device assembly which comprises a tissue-penetrating medical device, a cover for magnetizing the tissue-penetrating medical device including a sleeve member having a hollow body having a distal end and a proximal end to form a protective closure over at least a portion (e.g., a shaft) of tissue-penetrating medical device. In one or more embodiments, one or more magnets may be disposed on the sleeve member. In one or more embodiments, the sleeve member has a length to cover the shaft of the tissue-penetrating medical device, for example, a needle cannula. In one or more embodiments, the open end of the hollow tubular body provides a receiving space for receiving at least part of the tissue-penetrating medical device. In one or more embodiments, the tissue-penetrating medical device includes a needle assembly including a needle and the shaft, and when the shaft is magnetized, the tissue-penetrating medical device is configured for use in a procedural guidance system to locate and project a position of the shaft during an invasive medical procedure. In one or more embodiments, the medical device assembly further comprises a catheter having a proximal end and a distal end; a catheter adapter having a distal end, a proximal end, an overall length extending from the distal end to the proximal end, an internal cavity, an upper portion, a lower portion and a tip region having a distal opening having a circumference through which the catheter extends, the catheter adapter being connected to the proximal end of the catheter; and the shaft having a proximal end and a distal end, and the needle assembly includes a needle hub connected to the proximal end of the shaft, the needle hub including a hub magnet. In one or more embodiments, the catheter adapter is connected to the proximal end of the shaft.

A third aspect of the disclosure pertains to a method of magnetizing a tissue-penetrating medical device. The method includes positioning at least a shaft of the tissue-penetrating medical device in a cover including a receiving space, the cover including a magnet on the cover; and removing the tissue-penetrating medical device from the receiving space to magnetize the shaft of the tissue-penetrating medical device in said receiving space. The tissue-penetrating medical device is a needle, cannula, stylet, catheter, scalpel or guidewire. In one or more embodiments, the magnet is a collar surrounding the cover. Alternatively, the cover includes at least two magnets.

DETAILED DESCRIPTION

Before describing several exemplary embodiments of the disclosure, it is to be understood that the description provided is not limited to the details of construction or process steps set forth in the following description. The devices and methods described herein are capable of other embodiments and of being practiced or being carried out in various ways.

In this disclosure, a convention is followed wherein the distal end of the device is the end closest to a patient and the proximal end of the device is the end away from the patient and closest to a practitioner.

Aspects of the disclosure pertain to an improved system that addresses the challenges to the existing technology and systems to passively magnetize a needle, such as a needle used with a peripheral intravenous (IV) catheter. One or more embodiments of the present disclosure relate to a tissue-penetrating medical device with a needle cover with an integrated magnet on or within the needle cover. According to one or more embodiments, the device and system of the present disclosure passively and consistently magnetizes the needle. In one or more embodiments, passive magnetization of an invasive medical device is achieved with no additional or new clinical steps because the invasive medical device already includes a cover that covers the distal tip of the device. In one or more embodiments, the devices and systems described herein provide more precise control of the location of the magnet relative to the device to be magnetized, resulting in a more consist and predictable magnetic field applied to the invasive medical device. In one or more embodiments, the devices and methods described herein create no additional risk of needle damage compared to existing magnetizer devices and no additional risk for contamination compared to existing magnetizer devices.

Figure 2:
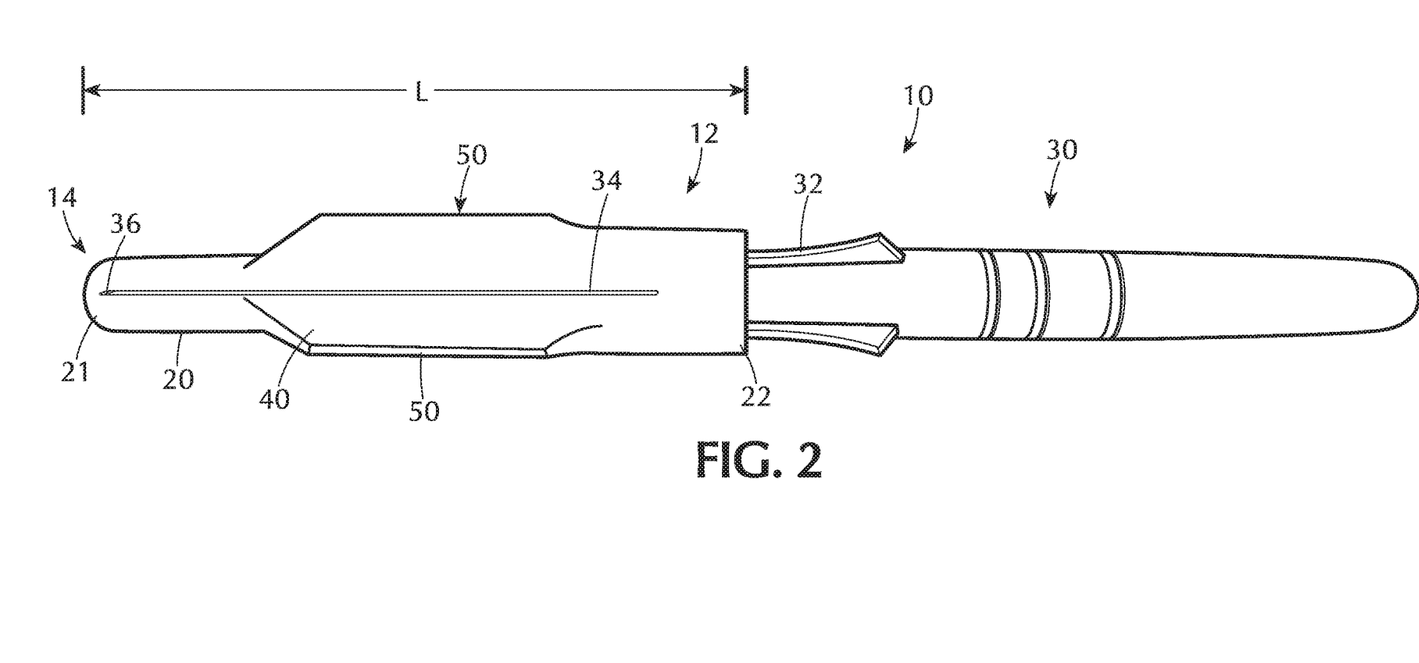
FIG. 2 shows a perspective view of an embodiment of a needle cover of the present disclosure.

Referring now to FIG. 2, showing one aspect of the disclosure pertains to a cover 12 for magnetizing a tissue-penetrating medical device 10 comprising a sleeve member 14 having a hollow body 20 having a distal end 21 and a proximal end 22 to form a protective closure over the shaft 34 of a tissue-penetrating medical device 30. In one or more embodiments, the hollow body 20 can be tubular or any other suitable shape. In the embodiment shown, the tissue-penetrating medical device 30 is shown as a needle assembly including a needle housing 32 and a shaft 34 of the needle having a sharp distal tip 36. It will be appreciated that in FIG. 2, the sleeve member 14 is shown as transparent and the shaft 34 of the tissue-penetrating medical device 30 is visible. The sleeve member 14 has a length L that covers the shaft 34 of the tissue-penetrating medical device 30, including the sharp distal tip 36 to prevent accidental needle sticks. The arrows shown in FIG. 2 with respect to the length "L" also show the longitudinal axis of the shaft 34. The open end 22 of the hollow body 20 provides a device-receiving space 40 for receiving at least the shaft 34 of the tissue-penetrating medical device 30. The cover 12 includes at least one magnet 50, and in the embodiment show, at least two magnets 50 disposed on the sleeve member 14.

The device-receiving space 40 is sized and shaped to permit movement of the shaft 34 of the tissue-penetrating medical device 30 into and out of the device-receiving space 40. In one embodiment, the device-receiving space 40 permits movement of the shaft 34 of the tissue-penetrating medical device 30 into the device-receiving space 40 in a movement that is parallel to the longitudinal axis of the shaft 34 of tissue-penetrating medical device 30. The cover 12 passively magnetizes the shaft 34 of the tissue-penetrating medical device 30 when the cover 12 is removed from the shaft 34 of the tissue-penetrating medical device.

Figure 3A:
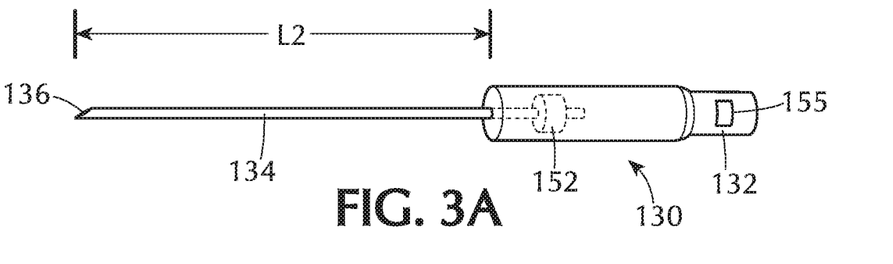
FIG. 3A shows an embodiment of a tissue-penetrating medical device prior to insertion into a needle cover of the present disclosure.
Figure 3B:
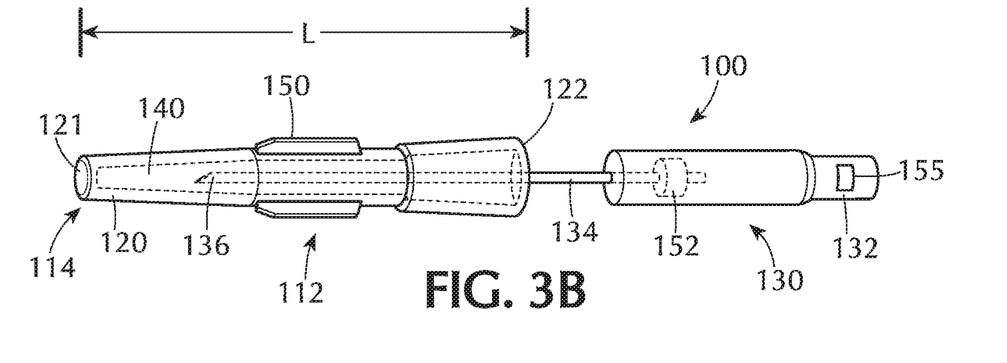
FIG. 3B shows an embodiment of a tissue-penetrating medical device partially inserted into a needle cover of the present disclosure.
Figure 3C:
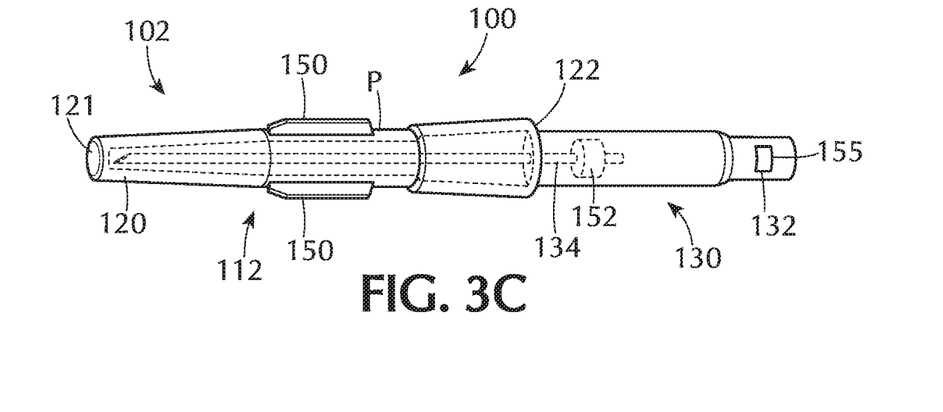
FIG. 3C shows an embodiment of a tissue-penetrating medical device fully inserted into a needle cover of the present disclosure.

FIGS. 3A to 3C show a medical device 100 including a tissue-penetrating medical device 130, a cover 112 for magnetizing the shaft 134 of the tissue-penetrating medical device 130. The cover 112 includes a sleeve member 114 having a hollow tubular body 120 having a distal end 121 and a proximal end 122 to form a protective closure over the shaft 134 of the tissue-penetrating medical device 130, the sleeve member 114 having a length L to cover the shaft 134 of the tissue-penetrating medical device 130, the shaft 134 having a length L2 and a distal tip 136. The open end 122 of the hollow tubular body 120 provides a receiving space 140 for receiving at least the shaft 134 of the tissue-penetrating medical device 130, and two magnets 150 on the sleeve member 134. It will be understood that while two magnets 150 are shown, the device is not limited to a particular number of magnets or to a particular location of the magnets around the sleeve member. Magnets 150 may be positioned in any position or orientation around the sleeve member. In one or more embodiments, a single magnet can be utilized to magnetize the shaft 134, or more than two magnets can be utilized.

In embodiments in which two magnets are utilized, the orientation of the magnetic fields of the two magnets can vary. One magnet can have north and south poles on axis with shaft of the tissue-penetrating medical device, while the second magnet can have north and south poles off-axis or perpendicular to the shaft of the tissue-penetrating medical device. Alternatively, the two magnets both can have north and south poles off axis with the shaft of the tissue-penetrating medical device, or the two magnets both can have north and south poles on axis with the shaft of the tissue-penetrating medical device.

FIG. 3A shows the tissue-penetrating medical device 130 prior to insertion into the cover 112 of the present disclosure. The tissue penetrating medical device 130 includes the shaft 134 having a length L2, a distal tip 136, and the shaft 134 is mounted to the housing 130 by a hub 152. In one or more embodiments, the hub 152 includes a hub magnet 155. In one or more embodiments, hub magnet 155 is a permanent fixed magnet. Hub magnet 155 may provide for a fixed magnetic reference point when the tissue-penetrating needle is used with a combination of ultrasound and magnetic technologies to provide visualization of subdermal anatomy and device position. FIG. 3B shows the shaft 134 of the tissue-penetrating medical device 130 partially inserted into a cover 112 of the present disclosure. FIG. 3C shows the shaft 134 of the tissue-penetrating medical 30 device fully inserted into a cover 112 of the present disclosure. The medical device 100 as shown in FIG. 3C can be packaged and ready for use for a medical procedure. The medical device 100 shown in FIG. 3C can be packaged together with other devices as part of a larger medical device assembly. Thus, FIG. 3C shows a medical device 100 which is a needle subassembly having a cover 112 having at least one magnet 150 configured to magnetize shaft 134 of the medical device 100 upon removal of the cover 112 from the shaft. The medical device 100 could further be packaged as part of a catheter assembly including a catheter adapter subassembly.

Figure 4:
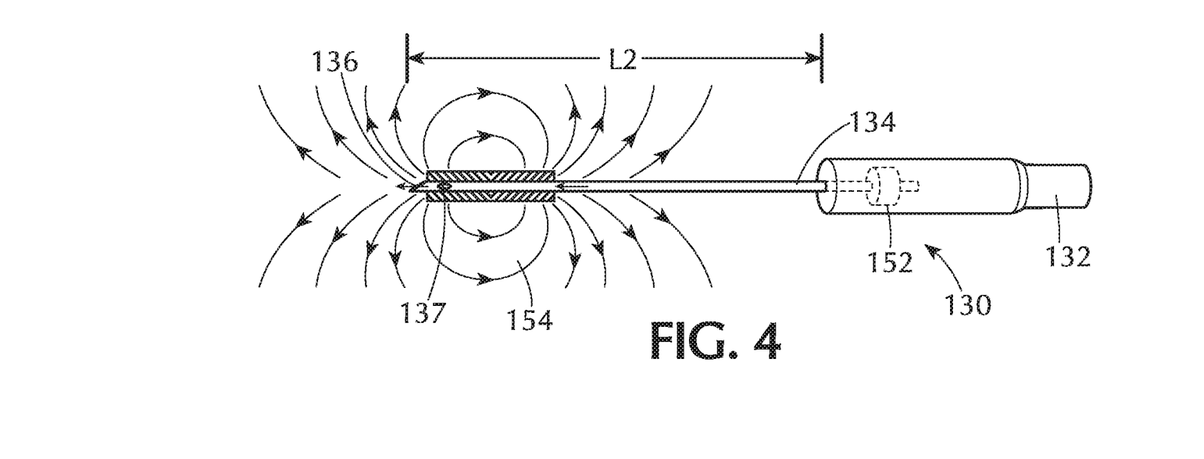
FIG. 4 shows an embodiment of a tissue-penetrating medical device fully magnetized after being removed from a needle cover of the present disclosure.

FIG. 4 shows the tissue-penetrating medical device 130 with the shaft 134 magnetized after the shaft 134 has been removed from the needle cover shown in FIGS. 3B-3C. As shown in FIGS. 3B-3C, two magnets 150 can be integrated into cover 112 so that the cover 112 passively magnetizes the shaft 134 upon removal of cover 112. The embodiment shown in FIGS. 3B-3C shows two magnets 150 positioned around cover 112. Such a cover could be easily integrated in existing catheter assemblies and other invasive medical devices such as guidewires and stylets to enable the magnetization of the shafts of various invasive medical devices upon removal of the cover to passively magnetize the shaft. The axial position of the magnets can be modified and positioned relative to the shaft length and the desired portion of the shaft to be magnetized. For example, in the case of a needle, the magnets can be specifically positioned based on the gauge and length of the needle. As shown in FIG. 3B, the positioning of the magnets would result in the shaft 134 being magnetized from the approximately the position P shown in FIG. 3 to the distal tip 136 of the shaft 134 as the portion of the shaft from P to the distal tip P will be will be moved through the magnetic field provided by the magnets 150. This the tissue-penetrating medical device 130 can now be used with a procedural guidance system that utilize magnetic sensors as a means of measuring and predicting needle tip location relative to the target anatomy. In one or more embodiments, the distal end of the tissue penetrating medical device 130 includes a notch 137 located on the distal tip 136 of the shaft 134 to provide immediate confirmation of vessel entry at a point of insertion.

Figure 5:
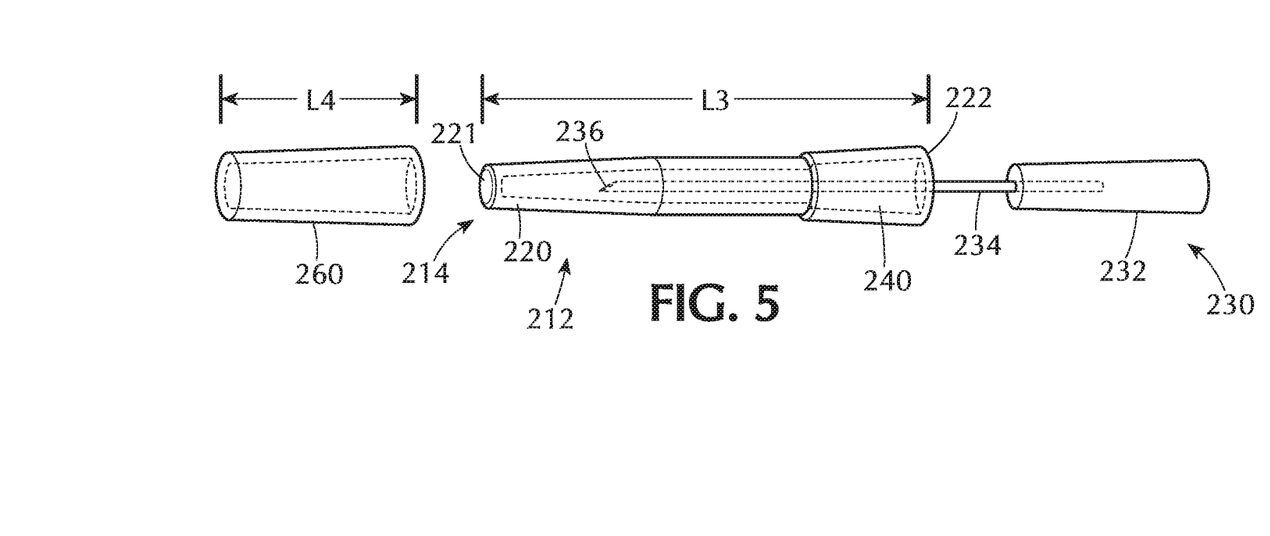
FIG. 5 shows an embodiment of a tissue-penetrating medical device with a magnetic collar.

FIG. 5 shows an embodiment of a tissue-penetrating medical device 230 including a cover 212 having a magnetizing collar 260, which can be a magnet in the shape of the collar 260 as shown. The cover 212 includes a sleeve member 214 having a hollow tubular body 220 having a distal end 221 and a proximal end 222 to form a protective closure over the shaft 234 of the tissue-penetrating medical device 230. The open end 222 of the hollow tubular body 220 provides a receiving space 240 for receiving at least the shaft 234 of the tissue-penetrating medical device 230. The magnetizing collar 260 is show as being disconnected from the cover 212, but the magnetizing collar 260 is variably positioned along the length L3 of the cover 212 relative to the shaft 234. The magnetizing collar 260 can be used as a single use disposable item, or the magnetizing collar 260 may be reusable since the needle cover stays in place during the magnetization step. Therefore, according to one or more embodiments, the magnetizing collar 260 is detachably mounted to the cover 212. In alterative embodiments, the magnetizing collar 260 is permanently mounted to the cover 260. The magnetizing collar 260 can be slidably moved along the length of the cover 212. In other embodiments, the length L4 of the magnetizing collar 260 may be equal to the length L3 of the cover 212 such that the entire shaft 234 of the tissue-penetrating medical device 230. In other embodiments, the length L4 of the magnetizing collar 260 is 10%, 20%, 30%, 40%, 50%, 60%, 70%, 80% or 90% of the length L3 of the cover 212. The magnetizing collar 260 can be a tubular magnet that substantially surrounds the periphery of the cover, or the magnetizing collar 260 can be a cover made of plastic or other material with an array of magnets substantially surrounding the periphery of the cover.

Figure 6A:
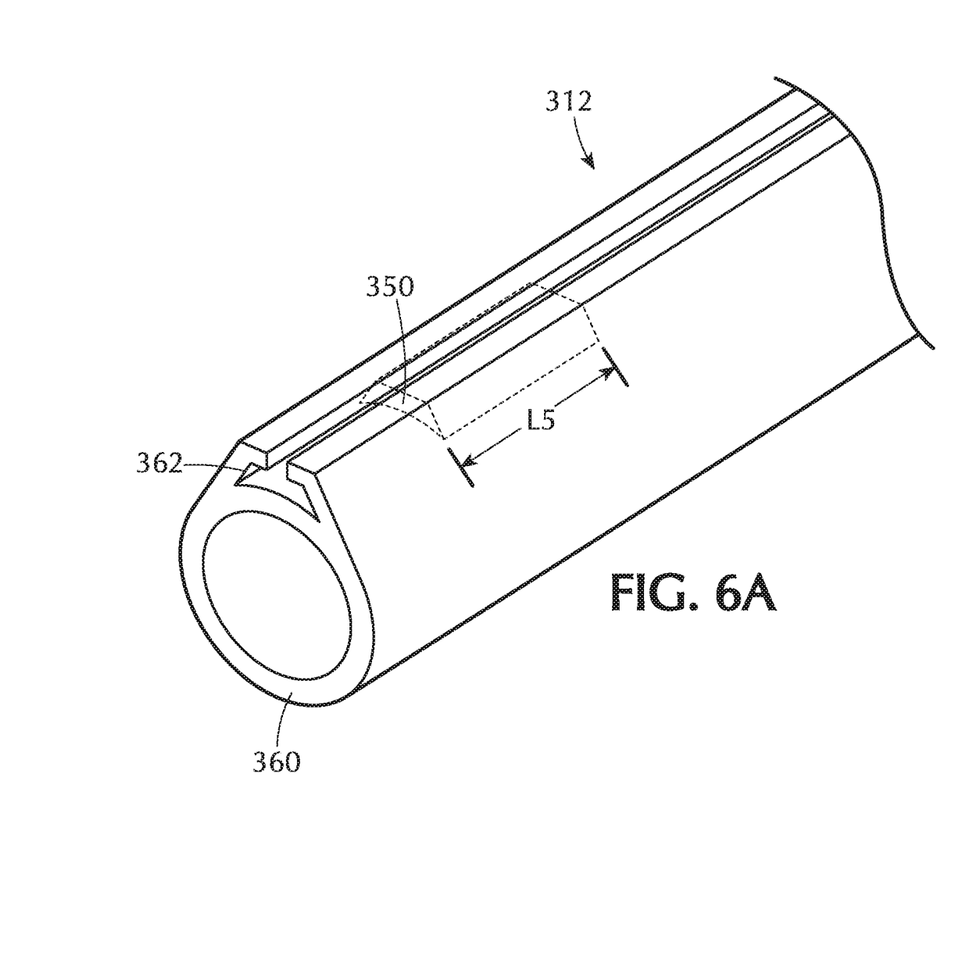
FIG. 6A shows a partial perspective view of a tip of a needle cover with an embedded magnet.
Figure 6B:
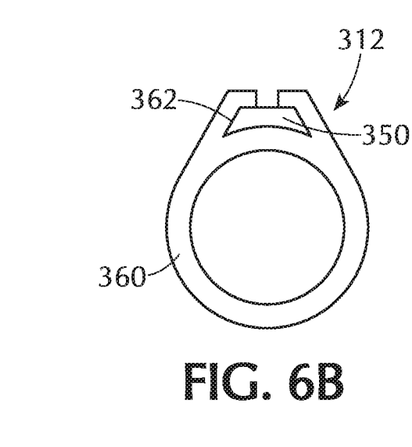
FIG. 6B shows an end view of a needle cover with one embedded magnet.
Figure 6C:
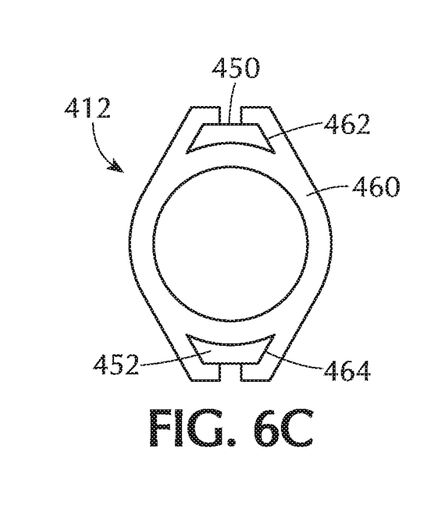
FIG. 6C shows an end view of a needle cover with two embedded magnets.

FIGS. 6A-6C show one way of integrating at least one magnet with a cover for a tissue-penetrating medical device. FIG. 6A shows a partial perspective view and FIG. 6B shows an end view of a cover 312 having an embedded magnetic 350 in the wall 360 of the cover 360. The magnet 350 is embedded in a slot 362. The magnet 350 can be sized to be slidably mounted within the slot 362 and held in place by friction fit, or the magnet can be attached with an adhesive or other suitable ways. Alternatively, the magnet 350 could be integrally molded into the wall 360 during the forming process for the cover 312. The length L5 of the magnet 350 shown in FIG. 6A is shown as being less than the length of the cover. According to one or more embodiments, the length L5 of the magnet 350 can be equal to the length of the cover, or 10%, 20%, 30%, 40%, 50%, 60%, 70%, 80% or 90% of the length of the cover.

FIG. 6C shows an embodiment of a cover 412 with a first magnet 450 in a first slot 462 of the wall 460 of the cover 412, and a second magnet 452 in a second slot 464 in the wall 460 of the cover. The first magnet 450 and second magnet 452 are shown as being positioned around the cover 412, for example, 180 degrees from each other. It will be understood that the two magnets can be in other positions with respect to each other. Additionally, the cover 412 can include more than two magnets. The first magnet 450 and second magnet 452 can be slidably mounted in the respective first slot 462 and the second slot 464 and held in place by friction fit, or they could be held in place by adhesive. In alternative embodiments, the magnets can be integrally molded with the cover 412. The two or more magnets may have oppositely oriented poles.

In alternative embodiments, a needle cover is provided that has geometric dimensions that permit the needle cover to be placed inside existing needle magnetizing devices while the needle cover is covering the shaft of the needle. The distal end of the needle cover may be used to limit the depth of insertion by providing a stop to contact the bottom of the needle magnetizing device. Alternatively, a feature near the proximal portion of the needle cover can be provided on the cover to limit the depth of insertion by a stop on the proximal opening of the needle magnetizer.

The covers described herein can have a variety of properties. In one or more embodiments, the covers are formed from plastic. In one or more embodiments, the covers are sterile. In one or more embodiments, the covers are disposable. In other embodiments, the covers may be both sterile and disposable.

The tissue-penetrating medical device may be a needle, catheter, introducer needle, stylet, scalpel or guidewire. In one embodiment, the tissue-penetrating medical device is a needle, which when magnetized can be used with a procedural guidance system to locate and project the position of the needle during an invasive medical procedure. The tissue-penetrating medical device according to one or more embodiments is includes a magnetizable metallic material. In a specific embodiment, the magnetizable metallic material is magnetizable stainless steel.

The covers described herein may also be incorporated into a vascular access device comprising a catheter, a catheter adapter subassembly, and a needle subassembly including an introducer needle, a needle hub connected to the proximal end of the introducer needle and a needle cover according to any of the embodiments described herein. The needle cover may include a plastic sleeve member having a hollow tubular body to form a protective closure over the introducer needle, and two or more magnets disposed on the needle cover as described herein.

An example of a medical device assembly, specifically a vascular access device including a catheter according to any of the foregoing embodiments described above is illustrated in FIG. 7. The medical device assembly 500 shown in FIG. 7 comprises a tissue penetrating medical device in the form of a needle subassembly 514, and a catheter adapter subassembly 512 including a catheter adapter body 516 and a catheter tubing 518 and a permanent magnet element 532. In one or more embodiments, the catheter adapter is connected to the proximal end of the shaft.

Permanent magnet element 532 may serve as an additional reference point when used in combination with ultrasound and magnetic technologies to provide visualization of subdermal anatomy and device position. A needle (not shown) within the catheter tubing 518 shows a magnetic portion 530, and the needle has been magnetized upon removal of a cap including a magnet as described with respect to FIGS. 2-7 herein. Magnetizing the needle with the cover as described herein creates a magnetic field 515 in the magnetic region 530.

Figure 7:
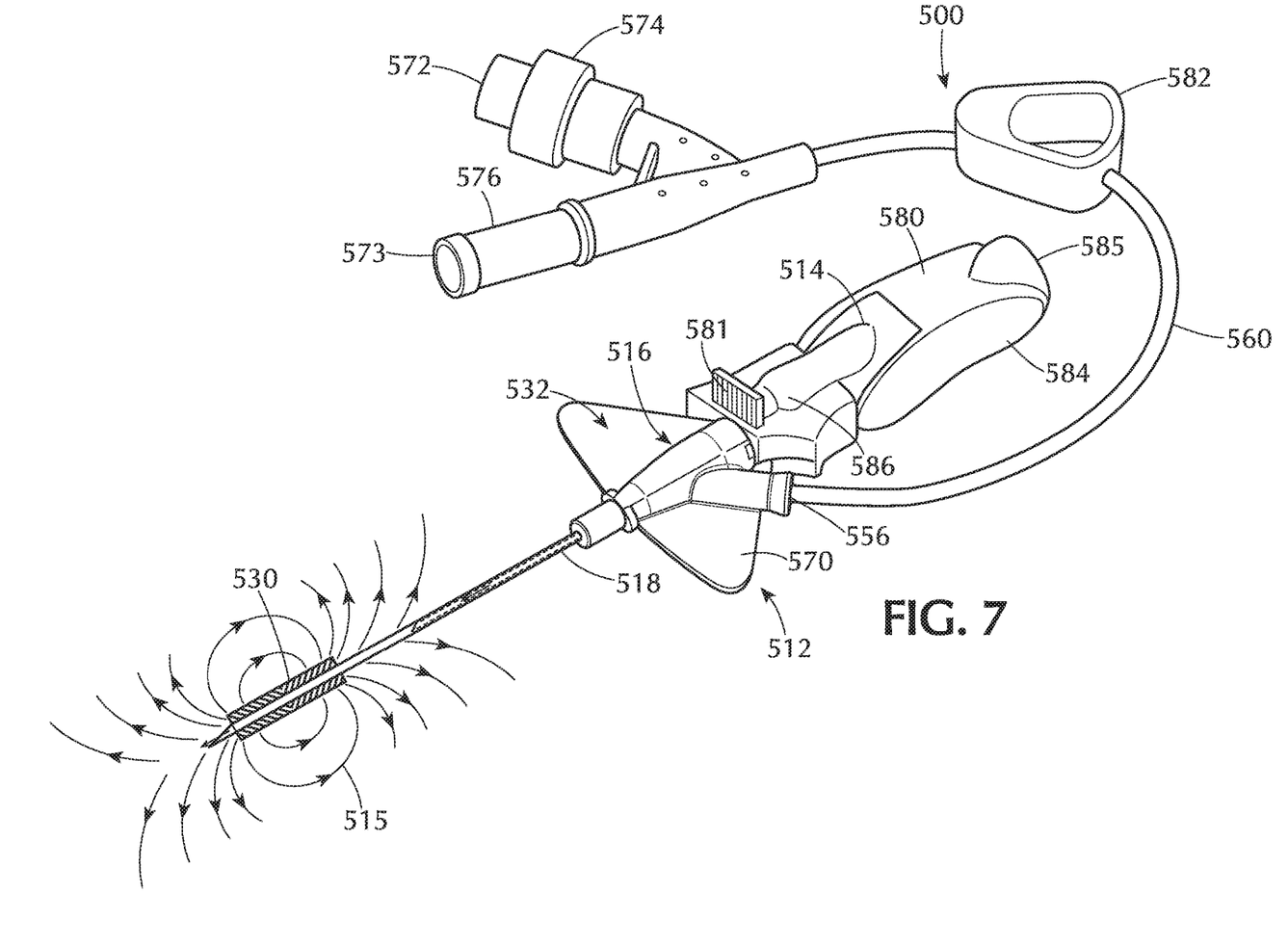
FIG. 7 shows an embodiment of a medical device.

The medical device 500 may be a vascular access device which includes a lateral access port 556 and may be connected to a section of an extension tube 560 for establishing fluid communication between an IV fluid source and the catheter tubing 518. In one or more embodiments, the extension tube 560 is built-in to reduce contamination and mechanical phlebitis by eliminating manipulation at the insertion site. In one or more embodiments, the extension tube 560 is compatible with high pressure injection. In one or more embodiments, the extension tube 560 provides continuous confirmation of vessel access during advancement of the catheter into the patient vein.

In one or more embodiments, a needle of a needle subassembly 514 is inserted into a lumen of the catheter tubing 518. The needle subassembly 514 is shown as including finger grips 584 positioned at the sides of the needle subassembly 514 to facilitate various insertion techniques. In one or more embodiments, bumps may be present on the finger grip to indicate where to the user may grip the device for needle removal. In one or more embodiments, a thumb pad 585, having a gently convex surface, is provided at the proximal end of the needle subassembly 514. A flange 586, having a gently convex surface, is provided at the proximal end of the needle subassembly 514 to provide a finger pad. A wing member 570, thumb pad 585 and flange 586 may be utilized by the user during insertion, permitting the user to elect which insertion technique to employ.

In one or more embodiments, the needle subassembly 514 includes a needle shield 580. The needle shield 580 may be a design adapted to secure the tip of the needle within the shield after use. In one or more embodiments, the needle shield 580 may be activated passively. The needle tip is completely covered by the needle shield 580 in a fixed position. In one or more embodiments, a ferrule, crimp or other structure may be included near the tip for engagement with a needle shield in certain applications.

A push tab 581 may be provided to facilitate catheter advancement during insertion. The push tab 581 also allows for one-handed or two-handed advancement. In one or more embodiments, the push tab 581 is removed with the needle shield 580. A clamp 582 may also be included on the extension tubing to prevent blood flow when replacing the access port.

In one or more embodiments, the vascular access device 500 further includes a first luer access 572 and a second luer access 573 in fluid communication with the extension tube 560, a blood control split septum 574 associated with the first luer access 572, and an air vent 576 associated with the second luer access 573. Split septum 574 allows for a reduction in catheter-related bloodstream infection (CRBSI) while providing unrestricted flow and a straight fluid path and functions as a blood control septum. In one or more embodiments, the split septum 574 may be located in an internal cavity of the catheter adapter or on the distal end of the catheter adapter. In yet another embodiment, the split septum 574 may be located on a distal end of the extension tube 560. The air vent 576 allows air to escape from the system during insertion, providing continuous confirmation of vascular access while preventing leakage of blood from the system during insertion. In one or more embodiments, the air vent 576 may be at the distal end of extension tube 560.

In one or more embodiments, the base unit can be integrated into the ultrasound system with the ultrasound processor and a magnetometric detector being in direct communication with the ultrasound system either via wireless link or using the same physical cable.

Another aspect of the disclosure pertains to a method of magnetizing a tissue-penetrating medical device. Embodiments of the method include positioning a shaft of the tissue-penetrating medical device in a cover including a device-receiving space, the cover including at least one magnet on the cover; removing the tissue-penetrating medical device from the device-receiving space to magnetize the shaft of the tissue-penetrating medical device.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A cover for magnetizing a tissue-penetrating medical device comprising:

a removable sleeve member comprising a hollow tubular body to form a protective closure over a shaft of a tissue-penetrating medical device prior to use, the sleeve member comprising a longitudinal axis, an open end of the hollow tubular body providing a receiving space for receiving at least the shaft of the tissue-penetrating medical device; and a first magnet slidably mounted within a first slot parallel to the longitudinal axis on the sleeve member and a second magnet slidably mounted within a second slot parallel to the longitudinal axis on the sleeve member, the first magnet and the second magnet disposed on the sleeve member effective to passively magnetize the shaft of the tissue-penetrating medical device when the sleeve member is removed from the shaft of a tissue-penetrating medical device;

wherein the slots and the first magnet and second magnet partially surround the receiving space, wherein the first magnet and second magnet are configured to slidably move to a location along a length of the cover providing control of the location of the magnet relative to the medical device, and once embedded at the location, the first magnet and second magnet are held at the location in the first slot and the second slot by a friction fit.

2. The cover of claim 1, wherein the receiving space permits movement of the shaft of the tissue-penetrating medical device in the receiving space in a direction parallel to the longitudinal axis of the tissue-penetrating medical device.

3. The cover of claim 1, wherein the first magnet and second magnet are on one side of the sleeve member.

4. The cover of claim 1, wherein the cover is sterile.

5. The cover of claim 1, wherein the cover is disposable.

6. The cover of claim 1, wherein the cover comprises plastic.

7. The cover of claim 1, wherein one magnet surrounds the cover.

8. The cover of claim 7, wherein the magnet is tubular.

* * * * *